(12) United States Patent
Choubey

(10) Patent No.: US 10,835,398 B2
(45) Date of Patent: Nov. 17, 2020

(54) MESHES AND DEVICES FOR TREATING VASCULAR DEFECTS

(71) Applicant: Covidien LP, Mansfield, MA (US)

(72) Inventor: Animesh Choubey, Lake Forest, CA (US)

(73) Assignee: COVIDIEN LP, Mansfield, MA (US)

(*) Notice: Subject to any disclaimer, the term of this patent is extended or adjusted under 35 U.S.C. 154(b) by 170 days.

(21) Appl. No.: 15/802,679

(22) Filed: Nov. 3, 2017

(65) Prior Publication Data
US 2019/0133795 A1 May 9, 2019

(51) Int. Cl.
*A61F 2/915* (2013.01)
*A61F 2/90* (2013.01)
*A61F 2/82* (2013.01)

(52) U.S. Cl.
CPC .............. *A61F 2/915* (2013.01); *A61F 2/90* (2013.01); *A61F 2002/823* (2013.01); *A61F 2002/9155* (2013.01); *A61F 2002/91533* (2013.01); *A61F 2002/91583* (2013.01); *A61F 2210/0076* (2013.01); *A61F 2240/001* (2013.01)

(58) Field of Classification Search
CPC .... A61F 2/915; A61F 2/07; A61F 2002/9155; A61F 2002/91575; A61F 2002/91558; A61F 2002/91566; A61F 2002/91583; A61F 2002/072; A61F 2002/077; A61F 2002/075
See application file for complete search history.

(56) References Cited

U.S. PATENT DOCUMENTS

| | | | | |
|---|---|---|---|---|
| 6,017,365 A | * | 1/2000 | Von Oepen | A61F 2/88 623/1.15 |
| 6,019,789 A | * | 2/2000 | Dinh | A61F 2/91 623/1.15 |
| 6,042,597 A | * | 3/2000 | Kveen | A61F 2/91 623/1.15 |
| 6,068,656 A | * | 5/2000 | Von Oepen | A61F 2/91 623/1.15 |

(Continued)

FOREIGN PATENT DOCUMENTS

| | | |
|---|---|---|
| EP | 2319575 B1 | 11/2013 |
| JP | 2004016668 | 1/2004 |

(Continued)

*Primary Examiner* — Diane D Yabut
(74) *Attorney, Agent, or Firm* — Fortem IP LLP; Mary Fox

(57) ABSTRACT

Devices that can be delivered into a vascular system to divert flow are disclose herein. According to some embodiments, devices are provided for treating aneurysms by diverting flow. An expandable device can comprise, for example, first a plurality of strut regions and a plurality of bridge regions. Each of the bridge regions may connect a first strut of a first strut region to a second strut of a second strut region. The first strut region may comprise a first plurality of apices defining a first circumferential plane, and the second strut region may comprise a second plurality of apices defining a second circumferential plane. A first curved segment of the bridge may extend across the first circumferential plane towards the first strut region, and a second curved segment of the bridge may extend across the second circumferential plane towards the second strut region.

19 Claims, 4 Drawing Sheets

(56) References Cited

U.S. PATENT DOCUMENTS

| | | | |
|---|---|---|---|
| 6,083,259 A * | 7/2000 | Frantzen | A61F 2/91 623/1.15 |
| 6,113,627 A * | 9/2000 | Jang | A61F 2/91 623/1.49 |
| 6,325,821 B1 * | 12/2001 | Gaschino | A61F 2/91 606/194 |
| 6,461,380 B1 * | 10/2002 | Cox | A61F 2/91 623/1.15 |
| 6,506,211 B1 * | 1/2003 | Skubitz | A61F 2/91 623/1.15 |
| 6,520,985 B1 | 2/2003 | Burpee et al. | |
| 6,527,919 B1 | 3/2003 | Roth et al. | |
| 6,579,310 B1 | 6/2003 | Cox et al. | |
| 6,679,910 B1 * | 1/2004 | Granada | A61F 2/91 623/1.15 |
| 6,761,731 B2 * | 7/2004 | Majercak | A61F 2/91 604/103.07 |
| 6,881,223 B2 | 4/2005 | Penn et al. | |
| 6,896,697 B1 * | 5/2005 | Yip | A61F 2/915 623/1.15 |
| 7,029,493 B2 * | 4/2006 | Majercak | A61F 2/91 606/194 |
| 7,060,089 B2 * | 6/2006 | Ley | A61F 2/844 606/196 |
| 7,169,174 B2 * | 1/2007 | Fischell | A61F 2/91 623/1.15 |
| 7,341,598 B2 * | 3/2008 | Davidson | A61F 2/82 623/1.16 |
| 7,722,661 B2 * | 5/2010 | Lenz | A61F 2/91 623/1.1 |
| 7,824,439 B2 * | 11/2010 | Toyokawa | A61F 2/91 623/1.15 |
| 7,867,272 B2 * | 1/2011 | Niermann | A61F 2/91 623/1.15 |
| 8,016,876 B2 | 9/2011 | Gregorich et al. | |
| 8,075,609 B2 | 12/2011 | Penn et al. | |
| 8,496,697 B2 * | 7/2013 | Obradovic | A61F 2/07 623/1.11 |
| 8,562,665 B2 | 10/2013 | Jang | |
| 8,603,014 B2 | 12/2013 | Alleman et al. | |
| 8,837,800 B1 | 9/2014 | Bammer et al. | |
| 8,915,950 B2 | 12/2014 | Cam et al. | |
| 8,940,003 B2 | 1/2015 | Slee et al. | |
| 9,119,656 B2 | 9/2015 | Bose et al. | |
| 9,126,018 B1 | 9/2015 | Garrison | |
| 9,180,031 B2 | 11/2015 | Vogel et al. | |
| 9,211,132 B2 | 12/2015 | Bowman | |
| 9,241,699 B1 | 1/2016 | Kume et al. | |
| 9,265,512 B2 | 2/2016 | Garrison et al. | |
| 9,308,007 B2 | 4/2016 | Cully et al. | |
| 9,399,118 B2 | 7/2016 | Kume et al. | |
| 9,445,828 B2 | 9/2016 | Turjman et al. | |
| 9,445,829 B2 | 9/2016 | Brady et al. | |
| 9,492,637 B2 | 11/2016 | Garrison et al. | |
| 9,539,022 B2 | 1/2017 | Bowman | |
| 9,561,345 B2 | 2/2017 | Garrison et al. | |
| 9,579,119 B2 | 2/2017 | Cully et al. | |
| 9,585,741 B2 | 3/2017 | Ma | |
| 9,603,732 B2 | 3/2017 | Ma et al. | |
| 9,642,635 B2 | 5/2017 | Vale et al. | |
| 9,655,633 B2 | 5/2017 | Leynov et al. | |
| 9,737,318 B2 | 8/2017 | Monstadt et al. | |
| 9,770,251 B2 | 9/2017 | Bowman et al. | |
| 9,801,643 B2 | 10/2017 | Hansen et al. | |
| 9,861,783 B2 | 1/2018 | Garrison et al. | |
| 9,993,257 B2 | 6/2018 | Losordo et al. | |
| 10,028,782 B2 | 7/2018 | Orion | |
| 10,029,008 B2 | 7/2018 | Creighton | |
| 10,039,906 B2 | 8/2018 | Kume et al. | |
| 2001/0049554 A1 * | 12/2001 | Ruiz | A61F 2/06 623/1.44 |
| 2002/0123798 A1 * | 9/2002 | Burgermeister | A61F 2/91 623/1.17 |
| 2003/0033007 A1 * | 2/2003 | Sirhan | A61F 2/91 623/1.42 |
| 2003/0069630 A1 * | 4/2003 | Burgermeister | A61F 2/91 623/1.15 |
| 2003/0176914 A1 | 9/2003 | Rabkin et al. | |
| 2004/0054399 A1 * | 3/2004 | Roth | A61F 2/91 623/1.16 |
| 2004/0054400 A1 * | 3/2004 | Granada | A61F 2/91 623/1.16 |
| 2004/0249446 A1 * | 12/2004 | Patel | A61F 2/91 623/1.16 |
| 2005/0209678 A1 | 9/2005 | Henkes et al. | |
| 2005/0261757 A1 * | 11/2005 | Shanley | A61F 2/915 623/1.15 |
| 2005/0288769 A1 * | 12/2005 | Globerman | A61F 2/91 623/1.15 |
| 2006/0222755 A1 * | 10/2006 | Diaz | A61F 2/91 427/2.21 |
| 2006/0235504 A1 * | 10/2006 | Gonzales | A61F 2/91 623/1.15 |
| 2007/0016283 A1 * | 1/2007 | Greenhalgh | A61F 2/07 623/1.15 |
| 2007/0050011 A1 * | 3/2007 | Klein | A61F 2/91 623/1.16 |
| 2007/0179590 A1 * | 8/2007 | Lu | A61F 2/07 623/1.16 |
| 2007/0239251 A1 * | 10/2007 | Prabhu | A61F 2/915 623/1.2 |
| 2008/0228261 A1 | 9/2008 | Anukhin et al. | |
| 2009/0036964 A1 * | 2/2009 | Heringes | A61F 2/91 623/1.2 |
| 2010/0023105 A1 | 1/2010 | Levy et al. | |
| 2011/0184452 A1 | 7/2011 | Huynh et al. | |
| 2011/0184453 A1 | 7/2011 | Levy et al. | |
| 2012/0209366 A1 * | 8/2012 | Sudo | A61F 2/91 623/1.11 |
| 2013/0030461 A1 | 1/2013 | Marks et al. | |
| 2013/0178928 A1 | 7/2013 | Vyas et al. | |
| 2013/0281788 A1 | 10/2013 | Garrison | |
| 2014/0114434 A1 * | 4/2014 | Cottone | A61F 2/04 623/23.69 |
| 2014/0276074 A1 | 9/2014 | Warner | |
| 2014/0277377 A1 | 9/2014 | Ischinger et al. | |
| 2014/0343595 A1 | 11/2014 | Monstadt et al. | |
| 2014/0379073 A1 * | 12/2014 | Wang | A61F 2/90 623/1.42 |
| 2015/0164665 A1 | 6/2015 | Cam et al. | |
| 2015/0359547 A1 | 12/2015 | Vale et al. | |
| 2016/0015402 A1 | 1/2016 | Brady et al. | |
| 2016/0015935 A1 | 1/2016 | Chan et al. | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113665 A1 | 4/2016 | Brady et al. | |
| 2016/0151618 A1 | 6/2016 | Powers et al. | |
| 2016/0157985 A1 | 6/2016 | Vo et al. | |
| 2016/0199620 A1 | 7/2016 | Pokorney et al. | |
| 2016/0235564 A1 | 8/2016 | Johnson et al. | |
| 2016/0296690 A1 | 10/2016 | Kume et al. | |
| 2016/0302808 A1 | 10/2016 | Loganathan et al. | |
| 2016/0375180 A1 | 12/2016 | Anzai | |
| 2017/0035589 A1 * | 2/2017 | Carpenter | A61F 2/013 |
| 2017/0079766 A1 | 3/2017 | Wang et al. | |
| 2017/0079767 A1 | 3/2017 | Leon-Yip | |
| 2017/0086862 A1 | 3/2017 | Vale et al. | |
| 2017/0100143 A1 | 4/2017 | Grandfield | |
| 2017/0105743 A1 | 4/2017 | Vale et al. | |
| 2017/0164963 A1 | 6/2017 | Goyal | |
| 2017/0215902 A1 | 8/2017 | Leynov et al. | |
| 2017/0224953 A1 | 8/2017 | Tran et al. | |
| 2017/0273692 A1 | 9/2017 | Choubey | |
| 2017/0273810 A1 | 9/2017 | Choubey | |
| 2017/0281909 A1 | 10/2017 | Northrop et al. | |
| 2017/0290599 A1 | 10/2017 | Youn et al. | |
| 2017/0333231 A1 * | 11/2017 | Li | A61L 27/04 |
| 2018/0049762 A1 | 2/2018 | Seip et al. | |
| 2018/0084982 A1 | 3/2018 | Yamashita et al. | |
| 2018/0116717 A1 | 5/2018 | Taff et al. | |

(56) References Cited

U.S. PATENT DOCUMENTS

| | | |
|---|---|---|
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| JP | 2005532887 | 11/2005 |
| JP | 2006026423 | 2/2006 |
| JP | 2006095095 | 4/2006 |
| JP | 2014004219 A | 1/2014 |
| JP | 2018118132 A | 8/2018 |
| KR | 20180102877 A | 9/2018 |
| WO | 2008005535 A2 | 1/2008 |
| WO | 2014153162 A1 | 9/2014 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

\* cited by examiner

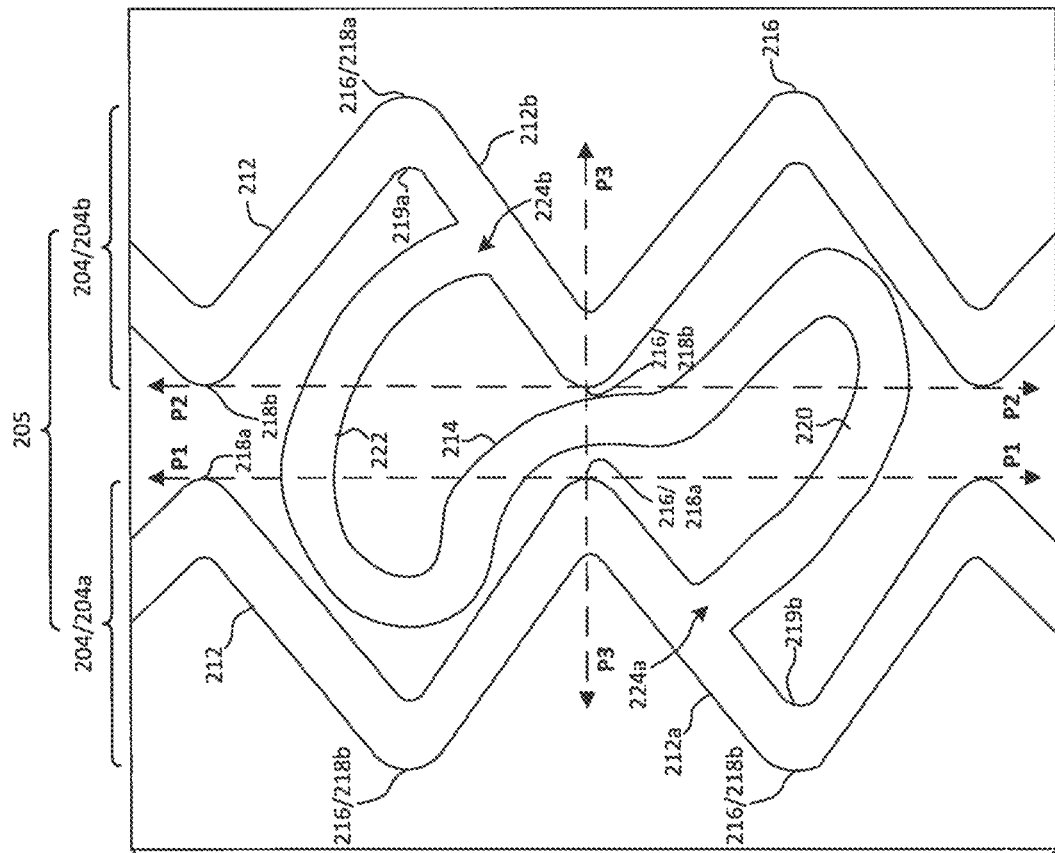
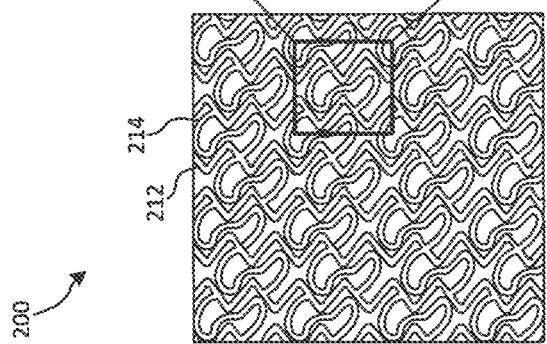
Figure 2B
Figure 2C

MESHES AND DEVICES FOR TREATING VASCULAR DEFECTS

TECHNICAL FIELD

The present technology relates generally to methods and devices for treating vascular defects, and particularly to diverting blood flow from a blood vessel into an aneurysm. Some embodiments of the present technology relate to flow-diverting mesh devices.

BACKGROUND

Aneurysms are an abnormal bulging or ballooning of a blood vessel that can result from the vessel wall being weakened by disease, injury, or a congenital abnormality. Aneurysms have thin, weak walls and tend to rupture, which can lead to stroke, death, disability, etc. One method of treating aneurysms includes inserting a flow-diverting stent or braid into a parent vessel that includes the aneurysm to be treated. Such stents or braids can be inserted into a vessel in a collapsed state, positioned next to the neck of the aneurysm, and expanded into apposition with the vessel wall. If the stent or braid has a sufficiently low porosity, it can function to block the flow of blood through the device and into the aneurysm to induce embolization of the aneurysm.

However, some aneurysms—and especially cerebral aneurysms—are located in small and tortuous portions of the vasculature. Current designs for flow-diverting stents or braids have difficulty achieving a snug fit across the neck of the aneurysm if the parent vessel is curved, twisted, or forked. For example, current designs generally suffer from crimping or kinking when positioned in such tortuous vessels. This can make it more difficult to position a flow-diverting device and can cause the device to have an inadequate porosity as the device is expanded within the vessel. Also, current designs often undesirably block blood flow to branching or secondary vessels that are close to the aneurysm. Accordingly, there exists a need for improved flow-diverting devices for treating aneurysms.

SUMMARY

Expandable devices can be delivered into vascular system to divert flow. According to some embodiments, expandable devices are provided for treating aneurysms by diverting flow. A flow-diverting expandable device can include two or more tubular meshes arranged coaxially. One or both of the tubular meshes may comprise a plurality of struts and/or bridges and be configured to be implanted in a blood vessel. The expandable device can be expandable to an expanded state at an aneurysm. The expandable device can have at least a section for spanning the neck of the aneurysm and a plurality of pores or openings located between the struts/bridges. The expandable device can have a sidewall and a plurality of pores/openings in the sidewall that are sized to inhibit flow of blood through the sidewall into an aneurysm to a degree sufficient to lead to thrombosis and healing of the aneurysm when the expandable device is positioned in a blood vessel and adjacent to the aneurysm. The subject technology is illustrated, for example, according to various aspects described below.

Further, some embodiments can provide a delivery system for treating an aneurysm. The system can comprise a microcatheter configured to be implanted into a blood vessel, a core member, extending within the microcatheter, having a distal segment, and the device extending along the core member distal segment.

The subject technology is illustrated, for example, according to various aspects described below. Various examples of aspects of the subject technology are described as numbered clauses (1, 2, 3, etc.) for convenience. These are provided as examples and do not limit the subject technology.

Clause 1. An expandable device comprising:
a plurality of strut regions extending circumferentially about the expandable device, each of the strut regions including a plurality of struts and a plurality of apices; and
a plurality of bridge regions extending between adjacent strut regions and including a plurality of bridges, wherein each of the bridges includes a first curved segment and a second curved segment having opposing concavities;
wherein each of the bridges connects a first strut of a first strut region to a second strut of a second strut region adjacent to the first strut region, the first strut region comprising a first plurality of apices extending towards the second strut region and defining a first circumferential plane, the second strut region comprising a second plurality of apices extending towards the first strut region and defining a second circumferential plane, with the first curved segment of the bridge extending across the first circumferential plane towards the first strut region, and the second curved segment of the bridge extending across the second circumferential plane towards the second strut region.

Clause 2. The expandable device of Clause 1 wherein the first strut is located on a first side of a first apex of the first strut region and the second strut is located on a second side of a second apex of the second strut region, the first and second apices being adjacent to each other, and the first side being opposite the second side.

Clause 3. The expandable device of Clause 1 or Clause 2 wherein the plurality of struts comprises a plurality of linear struts.

Clause 4. The expandable device of Clause 3 wherein each of the linear struts is coupled to an adjacent linear strut at one of the plurality of apices so as to form a zig-zag shape.

Clause 5. The expandable device of any one of Clauses 1-4 wherein the plurality of bridges comprises a plurality of s-shaped bridges.

Clause 6. The expandable device of any one of Clauses 1-5 wherein the first curved segment intersects the second circumferential plane at two different points, and wherein the second curved segment intersects the first circumferential plane at two different points.

Clause 7. The expandable device of any one of Clauses 1-6 wherein the bridge comprises a first end joined to the second strut and a second end opposite the first end and joined to the first strut, and wherein the first curved segment extends from the first end towards the first strut region, and the second curved segment extends from the second end towards the second strut region.

Clause 8. The expandable device of any one of Clauses 1-7 wherein each of the bridges is coupled to a strut region at a location away from the apices of the strut region.

Clause 9. The expandable device of any one of Clauses 1-8 wherein the expandable device is a mesh.

Clause 10. The expandable device of any one of Clauses 1-9 wherein the expandable device is a laser-cut sheet.

Clause 11. The expandable device of any one of Clauses 1-10 wherein the expandable device is non-braided.

Clause 12. The expandable device of any one of Clauses 1-11, wherein the expandable device is sized for deployment next to a vascular aneurysm, and wherein a sidewall of the expandable device has a pattern of struts and openings configured to inhibit flow of blood through the sidewall into the aneurysm to a degree sufficient to lead to thrombosis and healing of the aneurysm.

Clause 13. The expandable device of Clause 1, wherein the expandable device is sized for deployment next to a vascular aneurysm, and wherein a sidewall of the expandable device comprises means for inhibiting flow of blood through the sidewall into the aneurysm to a degree sufficient to lead to thrombosis and healing of the aneurysm.

Clause 14. The expandable device of Clause 1, wherein the expandable device comprises a thin film in which the strut regions and bridge regions are formed.

Clause 15. The expandable device of Clause 14, wherein the thin film is formed via a deposition process.

Clause 16. The expandable device of Clause 14, wherein the thin film comprises nitinol.

Clause 17. The expandable device of Clause 14, wherein the thin film comprises a metal or alloy, and a radiopaque material disposed on the metal or alloy.

Clause 18. The expandable device of Clause 17, wherein the radiopaque material is disposed only in areas of low stress concentration.

Clause 19. The expandable device of Clause 14, wherein the thin film is no more than 4 millimeters in maximum thickness.

Clause 20. A method comprising deploying the expandable device of any one of Clauses 1-19 in a blood vessel across an aneurysm and thereby inhibiting the flow of blood through a sidewall of the expandable device into the aneurysm to a degree sufficient to lead to thrombosis and healing of the aneurysm.

Clause 21. An expandable device comprising:
a first tubular mesh defining a lumen therethrough, the first tubular mesh comprising:
a plurality of strut regions extending circumferentially about the expandable device, each of the strut regions including a plurality of struts and a plurality of apices,
a plurality of bridge regions extending between adjacent strut regions and including a plurality of bridges, wherein each of the bridges includes a first indented segment and a second indented segment having opposing indentions; and
wherein each of the bridges connects a first strut of a first strut region to a second strut of a second strut region adjacent to the first strut region, the first strut region comprising a first plurality of apices extending towards the second strut region and defining a first circumferential plane, the second strut region comprising a second plurality of apices extending towards the first strut region and defining a second circumferential plane, with the first indented segment of the bridge extending across the first circumferential plane towards the first strut region, and the second indented segment of the bridge extending across the second circumferential plane towards the second strut region; and
a second tubular mesh, at least a portion of which is positioned within the lumen of the first tubular mesh.

Clause 22. The expandable device of Clause 21 wherein both of the first tubular mesh and the second tubular mesh are non-braided.

Clause 23. The expandable device of Clause 21 wherein the second tubular mesh is a tubular weave.

Clause 24. The expandable device of Clause 23 wherein the tubular weave is formed of a single wire.

Clause 25. The expandable device of Clause 21 wherein the second tubular mesh is a braid.

Clause 26. The expandable device of Clause 21 wherein the first tubular mesh is a laser-cut sheet.

Clause 27. The expandable device of Clause 21, wherein the expandable device is sized for deployment next to a vascular aneurysm, and wherein a sidewall of the expandable device has a pattern of struts and openings configured to inhibit flow of blood through the sidewall into the aneurysm to a degree sufficient to lead to thrombosis and healing of the aneurysm.

Clause 28. The expandable device of Clause 21, wherein the expandable device is sized for deployment next to a vascular aneurysm, and wherein a sidewall of the expandable device comprises means for inhibiting flow of blood through the sidewall into the aneurysm to a degree sufficient to lead to thrombosis and healing of the aneurysm.

Clause 29. The expandable device of Clause 21, wherein the expandable device comprises a thin film in which the strut regions and bridge regions are formed.

Clause 30. The expandable device of Clause 29, wherein the thin film is formed via a deposition process.

Clause 31. The expandable device of Clause 29, wherein the thin film comprises nitinol.

Clause 32. The expandable device of Clause 29, wherein the thin film comprises a metal or alloy, and a radiopaque material disposed on the metal or alloy.

Clause 33. The expandable device of Clause 32, wherein the radiopaque material is disposed only in areas of low stress concentration.

Clause 34. The expandable device of Clause 29, wherein the thin film is no more than 4 millimeters in maximum thickness.

Clause 35. A method comprising deploying any one of the expandable devices of Clauses 21-34 in a blood vessel across an aneurysm and thereby inhibiting the flow of blood through a sidewall of the expandable device into the aneurysm to a degree sufficient to lead to thrombosis and healing of the aneurysm.

Clause 36. An expandable device comprising:
a plurality of strut regions extending circumferentially about the expandable device, each of the strut regions including a plurality of struts that form a plurality of circumferentially disposed closed polygonal cells defined by the struts, wherein each of the struts is coupled to another strut at an apex; and
a plurality of bridge regions extending between adjacent strut regions and including a plurality of bridges, wherein each of the bridges comprises a first end and a second end opposite the first end, the first end being coupled to a first closed polygonal cell of a first strut region at a location away from apices of the first strut region, and the second end being coupled to a second closed polygonal cell of a second strut region adjacent to the first strut region at a location away from apices of the second strut region.

Clause 37. The expandable device of Clause 36 wherein at least one of the first closed polygonal cell and the second closed polygonal cell is a quadrilateral.

Clause 38. The expandable device of Clause 36 wherein the plurality of closed polygonal cells comprises a plurality of diamond-shaped cells.

Clause 39. The expandable device of Clause 36 wherein, within the individual strut regions, each closed polygonal cell is coupled to an adjacent closed polygonal cell at one of the apices.

Clause 40. The expandable device of Clause 36 wherein the plurality of bridges comprises a plurality of sinusoidal bridges.

Clause 41. The expandable device of Clause 36 wherein the expandable device is a mesh.

Clause 42. The expandable device of Clause 36 wherein the expandable device is a laser-cut sheet.

Clause 43. The expandable device of Clause 36, wherein the expandable device is sized for deployment next to a vascular aneurysm, and wherein a sidewall of the expandable device has a pattern of struts and openings configured to inhibit flow of blood through the sidewall into the aneurysm to a degree sufficient to lead to thrombosis and healing of the aneurysm.

Clause 44. The expandable device of Clause 36, wherein the expandable device is sized for deployment next to a vascular aneurysm, and wherein a sidewall of the expandable device comprises means for inhibiting flow of blood through the sidewall into the aneurysm to a degree sufficient to lead to thrombosis and healing of the aneurysm.

Clause 45. The expandable device of Clause 36, wherein the expandable device comprises a thin film in which the strut regions and bridge regions are formed.

Clause 46. The expandable device of Clause 37, wherein the thin film is formed via a deposition process.

Clause 47. The expandable device of Clause 37, wherein the thin film comprises nitinol.

Clause 48. The expandable device of Clause 37, wherein the thin film comprises a metal or alloy, and a radiopaque material disposed on the metal or alloy.

Clause 49. The expandable device of Clause 40, wherein the radiopaque material is disposed only in areas of low stress concentration.

Clause 50. The expandable device of Clause 37, wherein the thin film is no more than 4 millimeters in maximum thickness.

Clause 51. A method comprising deploying any one of the expandable devices of Clauses 36-50 in a blood vessel across an aneurysm and thereby inhibiting the flow of blood through a sidewall of the expandable device into the aneurysm to a degree sufficient to lead to thrombosis and healing of the aneurysm.

Clause 52. An expandable device comprising:
a first tubular mesh defining a lumen therethrough, the first tubular mesh comprising:
a plurality of strut regions extending circumferentially about the expandable device, each of the strut regions including a plurality of struts that form a plurality of circumferentially disposed closed polygonal cells defined by the struts, wherein each of the struts is coupled to another strut at an apex,
a plurality of bridge regions extending between adjacent strut regions and including a plurality of bridges, wherein each of the bridges comprises a first end and a second end opposite the first end, the first end being coupled to a first closed polygonal cell of a first strut region at a location away from apices of the first strut region, and the second end being coupled to a second closed polygonal cell of a second strut region adjacent to the first strut region at a location away from apices of the second strut region; and
a second tubular mesh, wherein at least a portion of the second tubular mesh is positioned within the lumen of the first tubular mesh.

Clause 53. The expandable device of Clause 52 wherein both of the first tubular mesh and the second tubular mesh are non-braided.

Clause 54. The expandable device of Clause 52 wherein the second tubular mesh is a tubular weave.

Clause 55. The expandable device of Clause 54 wherein the tubular weave is formed of a single wire.

Clause 56. The expandable device of Clause 52 wherein the second tubular mesh is a braid.

Clause 57. The expandable device of Clause 52 wherein the first tubular mesh is a laser-cut sheet.

Clause 58. The expandable device of Clause 52, wherein the expandable device is sized for deployment next to a vascular aneurysm, and wherein a sidewall of the expandable device has a pattern of struts and openings configured to inhibit flow of blood through the sidewall into the aneurysm to a degree sufficient to lead to thrombosis and healing of the aneurysm.

Clause 59. The expandable device of Clause 52, wherein the expandable device is sized for deployment next to a vascular aneurysm, and wherein a sidewall of the expandable device comprises means for inhibiting flow of blood through the sidewall into the aneurysm to a degree sufficient to lead to thrombosis and healing of the aneurysm.

Clause 60. The expandable device of Clause 52, wherein the expandable device comprises a thin film in which the strut regions and bridge regions are formed.

Clause 61. The expandable device of Clause 60, wherein the thin film is formed via a deposition process.

Clause 62. The expandable device of Clause 60, wherein the thin film comprises nitinol.

Clause 63. The expandable device of Clause 60, wherein the thin film comprises a metal or alloy, and a radiopaque material disposed on the metal or alloy.

Clause 64. The expandable device of Clause 63, wherein the radiopaque material is disposed only in areas of low stress concentration.

Clause 65. The expandable device of Clause 60, wherein the thin film is no more than 4 millimeters in maximum thickness.

Clause 66. A method comprising deploying any one of the expandable devices of Clauses 52-66 in a blood vessel across an aneurysm and thereby inhibiting the flow of blood through a sidewall of the expandable device into the aneurysm to a degree sufficient to lead to thrombosis and healing of the aneurysm.

Clause 67. An expandable device comprising:
a plurality of strut regions extending circumferentially about the expandable device, each of the strut regions including a plurality of struts and a plurality of apices; and
a plurality of bridge regions extending between adjacent strut regions and including a plurality of bridges,
wherein each of the bridges connects a first strut of a first strut region to a second strut of a second strut region adjacent to the first strut region, the first strut region comprising a first plurality of apices extending towards the second strut region, the second strut region comprising a second plurality of apices extending towards the first strut region, wherein the first strut is located on a first side of a first apex of the first strut region and the second strut is located on a second side of a second apex of the second strut region, the first and second apices being adjacent to each other, and the first side being opposite the second side.

Clause 68. The expandable device of Clause 67 wherein each of the bridges includes a first curved segment and a second curved segment having opposing concavities.

Clause 69. The expandable device of Clause 68 wherein the first plurality of apices define a first circumferential plane and the second plurality of apices define a second circumferential plane, wherein the first curved segment of the bridge extending across the first circumferential plane towards the first strut region, and the second curved segment of the bridge extending across the second circumferential plane towards the second strut region.

Clause 70. The expandable device of Clause 67 wherein each of the bridges includes a first indented segment and a second indented segment having opposing indentions.

Clause 71. The expandable device of Clause 70 wherein the first plurality of apices define a first circumferential plane and the second plurality of apices define a second circumferential plane, wherein the first indented segment of the bridge extending across the first circumferential plane towards the first strut region, and the second indented segment of the bridge extending across the second circumferential plane towards the second strut region.

Clause 72. The expandable device of Clause 67 wherein the plurality of struts comprises a plurality of linear struts.

Clause 73. The expandable device of Clause 72 wherein each of the linear struts is coupled to an adjacent linear strut at one of the plurality of apices so as to form a zig-zag shape.

Clause 74. The expandable device of Clause 67 wherein the plurality of bridges comprises a plurality of s-shaped bridges.

Clause 75. The expandable device of Clause 67 wherein the first curved segment intersects the second circumferential plane at two different points, and wherein the second curved segment intersects the first circumferential plane at two different points.

Clause 76. The expandable device of Clause 67 wherein the bridge comprises a first end joined to the second strut and a second end opposite the first end and joined to the first strut, and wherein the first curved segment extends from the first end towards the first strut region, and the second curved segment extends from the second end towards the second strut region.

Clause 77. The expandable device of Clause 67 wherein each of the bridges is coupled to a strut region at a location away from the apices of the strut region.

Clause 78. The expandable device of Clause 67 wherein the expandable device is a mesh.

Clause 79. The expandable device of Clause 67 wherein the expandable device is a laser-cut sheet.

Clause 80. The expandable device of Clause 67 wherein the expandable device is non-braided.

Clause 81. The expandable device of Clause 67, wherein the expandable device is sized for deployment next to a vascular aneurysm, and wherein a sidewall of the expandable device has a pattern of struts and openings configured to inhibit flow of blood through the sidewall into the aneurysm to a degree sufficient to lead to thrombosis and healing of the aneurysm.

Clause 82. The expandable device of Clause 67, wherein the expandable device is sized for deployment next to a vascular aneurysm, and wherein a sidewall of the expandable device comprises means for inhibiting flow of blood through the sidewall into the aneurysm to a degree sufficient to lead to thrombosis and healing of the aneurysm.

Clause 83. The expandable device of Clause 67, wherein the expandable device comprises a thin film in which the strut regions and bridge regions are formed.

Clause 84. The expandable device of Clause 83, wherein the thin film is formed via a deposition process.

Clause 85. The expandable device of Clause 83, wherein the thin film comprises nitinol.

Clause 86. The expandable device of Clause 83, wherein the thin film comprises a metal or alloy, and a radiopaque material disposed on the metal or alloy.

Clause 87. The expandable device of Clause 86, wherein the radiopaque material is disposed only in areas of low stress concentration.

Clause 88. The expandable device of Clause 83, wherein the thin film is no more than 4 millimeters in maximum thickness.

Clause 89. A method comprising deploying any one of the expandable devices of Clauses 67-89 in a blood vessel across an aneurysm and thereby inhibiting the flow of blood through a sidewall of the expandable device into the aneurysm to a degree sufficient to lead to thrombosis and healing of the aneurysm.

Clause 90. An expandable device comprising:
  a first tubular mesh defining a lumen therethrough, the first tubular mesh comprising:
    a plurality of strut regions extending circumferentially about the expandable device, each of the strut regions including a plurality of struts and a plurality of apices,
    a plurality of bridge regions extending between adjacent strut regions and including a plurality of bridges; and
    wherein each of the bridges connects a first strut of a first strut region to a second strut of a second strut region adjacent to the first strut region, the first strut region comprising a first plurality of apices extending towards the second strut region, the second strut region comprising a second plurality of apices extending towards the first strut region, wherein the first strut is located on a first side of a first apex of the first strut region and the second strut is located on a second side of a second apex of the second strut region, the first and second apices being adjacent to each other, and the first side being opposite the second side; and
  a second tubular mesh, at least a portion of which is positioned within the lumen of the first tubular mesh.

Clause 91. The expandable device of Clause 90 wherein each of the bridges includes a first curved segment and a second curved segment having opposing concavities.

Clause 92. The expandable device of Clause 91 wherein the first plurality of apices define a first circumferential plane and the second plurality of apices define a second circumferential plane, wherein the first curved segment of the bridge extending across the first circumferential plane towards the first strut region, and the second curved segment of the bridge extending across the second circumferential plane towards the second strut region.

Clause 93. The expandable device of Clause 90 wherein each of the bridges includes a first indented segment and a second indented segment having opposing indentions.

Clause 94. The expandable device of Clause 93 wherein the first plurality of apices define a first circumferential plane and the second plurality of apices define a second circumferential plane, wherein the first indented segment of the bridge extending across the first circumferential plane towards the first strut region, and the second indented segment of the bridge extending across the second circumferential plane towards the second strut region.

Clause 95. The expandable device of Clause 90 wherein both of the first tubular mesh and the second tubular mesh are non-braided.

Clause 96. The expandable device of Clause 90 wherein the second tubular mesh is a tubular weave.

Clause 97. The expandable device of Clause 96 wherein the tubular weave is formed of a single wire.

Clause 98. The expandable device of Clause 90 wherein the second tubular mesh is a braid.

Clause 99. The expandable device of Clause 90 wherein the first tubular mesh is a laser-cut sheet.

Clause 100. The expandable device of Clause 90, wherein the expandable device is sized for deployment next to a vascular aneurysm, and wherein a sidewall of the expandable device has a pattern of struts and openings configured to inhibit flow of blood through the sidewall into the aneurysm to a degree sufficient to lead to thrombosis and healing of the aneurysm.

Clause 101. The expandable device of Clause 90, wherein the expandable device is sized for deployment next to a vascular aneurysm, and wherein a sidewall of the expandable device comprises means for inhibiting flow of blood through the sidewall into the aneurysm to a degree sufficient to lead to thrombosis and healing of the aneurysm.

Clause 102. The expandable device of Clause 90, wherein the expandable device comprises a thin film in which the strut regions and bridge regions are formed.

Clause 103. The expandable device of Clause 102, wherein the thin film is formed via a deposition process.

Clause 104. The expandable device of Clause 102, wherein the thin film comprises nitinol.

Clause 105. The expandable device of Clause 102, wherein the thin film comprises a metal or alloy, and a radiopaque material disposed on the metal or alloy.

Clause 106. The expandable device of Clause 105, wherein the radiopaque material is disposed only in areas of low stress concentration.

Clause 107. The expandable device of Clause 102, wherein the thin film is no more than 4 millimeters in maximum thickness.

Clause 108. A method comprising deploying any one of the expandable devices of Clauses 90-107 in a blood vessel across an aneurysm and thereby inhibiting the flow of blood through a sidewall of the expandable device into the aneurysm to a degree sufficient to lead to thrombosis and healing of the aneurysm.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIGS. 2B and 2C are enlarged views of portions of the second mesh as shown in FIG. 2A. In FIG. 2C, the bridges attached to the struts shown in the enlarged view have been removed for ease of illustration.

In FIG. 3A, the bridges attached to the struts shown in the enlarged view have been removed for ease of illustration.

DETAILED DESCRIPTION

In the following detailed description, specific details are set forth to provide an understanding of the present technology. However, the present technology may be practiced without some of these specific details. In some instances, well-known structures and techniques have not been shown in detail so as not to obscure the present technology.

The terminology used in the description presented below is intended to be interpreted in its broadest reasonable manner, even though it is being used in conjunction with a detailed description of certain specific embodiments of the disclosure. Certain terms may even be emphasized below; however, any terminology intended to be interpreted in any restricted manner will be overtly and specifically defined as such in this Detailed Description section.

Aspects of the present disclosure are directed generally toward devices that can be delivered into a vascular system to divert flow. According to some embodiments, such devices are provided for treating aneurysms by diverting flow. For example, a device according to the present technology can be configured to interfere with blood flow to generally reduce the exchange of blood between a parent vessel and an aneurysm, which can induce thrombosis of the aneurysm. A device (or a device component, such as a frame and/or mesh) that interferes with blood flow in this manner can be said to have a "flow diverting" property.

Figure 1:
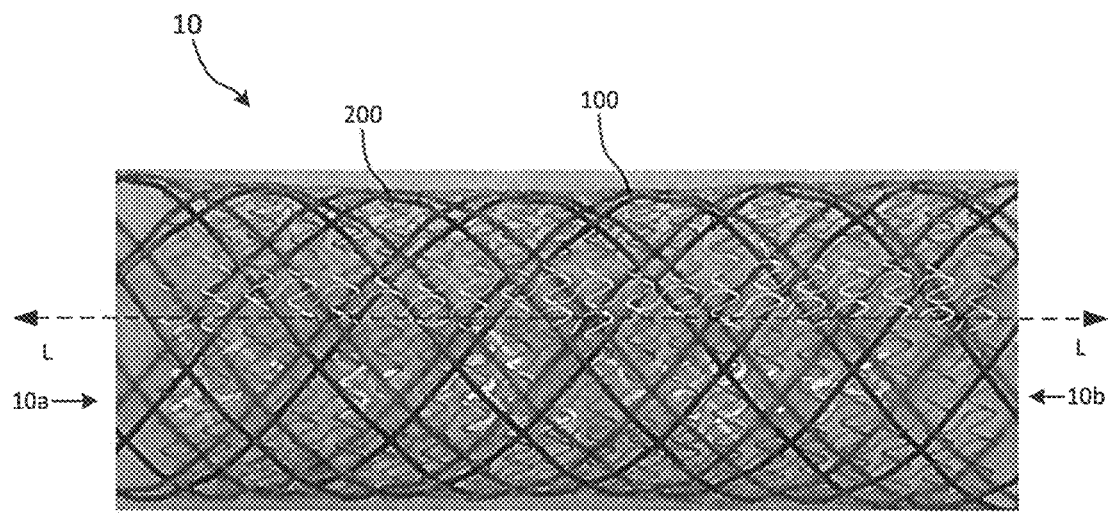
FIG. 1 is a schematic illustration of a flow-diverting device in accordance with the present technology, showing the device in a tubular configuration.

FIG. 1 is a side view of a flow-diverting device 10 (or "device 10") in an expanded, unconstrained state. As shown in FIG. 1A, the device 10 is a generally tubular structure configured to be positioned within a blood vessel lumen. For example, the device 10 may be configured to be implanted in a blood vessel lumen in the expanded state such that at least a portion of the device 10 spans the neck of an aneurysm. The device 10 has a first end 10a, a second end 10b opposite the first end 10a, and a central longitudinal axis L extending between the first and second ends 10a, 10b. As used herein, the term "longitudinal" can refer to a direction along an axis that extends through the lumen of the device while in a tubular configuration, and the term "circumferential" can refer to a direction along an axis that is orthogonal to the longitudinal axis and extends around the circumference of the device when in a tubular configuration.

The device 10 can include a first mesh 100 (or "mesh 100") and a second mesh 200 (or "mesh 200") disposed on and/or around the first mesh 100 such that the second mesh 200 is farther from the central longitudinal axis L of the device 10 than the first mesh 100. In some embodiments, the device 10 does not include the first mesh 100 and only includes the second mesh 200. An inner surface of the first mesh 100 defines a lumen extending through the device 10. As described in greater detail below, the first mesh 100 can be configured to stabilize and provide structural support to the device 10, while the second mesh 200 can be configured to divert blood flow away from the aneurysm and/or promote endothelialization with the blood vessel wall.

The first mesh 100 may be a self-expanding, porous, tubular structure formed of a single interwoven filament, a plurality of braided filaments, a laser-cut metal, a thin film formed via a deposition process, and other suitable porous structures. As shown in FIG. 1, in some embodiments the first mesh 100 is a non-braided, tubular weave. As used herein, "weave" or "tubular weave" refers to a single, continuous filament wound about an axis in a first longitudinal direction then a second, opposite longitudinal direction such that the filament overlaps itself at multiple locations along the length of the weave.

The second mesh 200 may be a non-braided, self-expanding tubular structure formed by thin film deposition. Examples of second meshes 200 for use with the flow-diverting devices of the present technology are discussed in greater detail below with reference to FIGS. 2A-2C and 3A-3B.

The first and second meshes 100, 200 can be formed using known flexible and/or superelastic materials such as nitinol, stainless steel, cobalt-chromium alloys (e.g., 35N LT® (Fort Wayne Metals, Fort Wayne, Ind.)), Elgiloy, magnesium alloys, tungsten, tantalum, platinum, or combinations thereof, or one or more polymers, or combinations of polymers and metals. In some embodiments, the first mesh 100 may include one or more drawn-filled tube ("DFT") wires comprising an inner material surrounded by a different outer material. The inner material, for example, may be radiopaque material, and the outer material may be a superelastic material.

The first mesh 100 may have a diameter in the unconstrained, expanded state (not shown) that is slightly larger than the diameter of the second mesh 200 in the unconstrained, expanded state. As such, when the device 10 is in an expanded, unconstrained state (as shown in FIG. 1), all or a portion of the outer surface of the first mesh 100 may be in contact with and/or pressing radially outwardly on all or a portion of the inner surface of the second mesh 200. In some embodiments, the first mesh 100 may be configured to have a greater chronic outward force (i.e., the outward force exerted by the first mesh when expanding from a low-profile, constrained state) and/or a greater radial force (i.e., outward force exerted by the vessel-engaging member during compression of the vessel-engaging member) than the second mesh 200. For example, the first mesh 100 may have a greater average sidewall thickness and/or a greater average pore size and/or a greater average filament thickness or strut thickness than the second mesh 200, both of which may provide increased chronic outward force and radial force. In other embodiments, the second mesh 200 may have a greater sidewall thickness and/or a greater pore size than the first mesh 100, and in some embodiments the first and second meshes 100, 200 may have generally the same sidewall thickness and/or pore size.

Referring still to FIG. 1, the length of the first mesh 100 may be greater than the length of the second mesh 200 so that the first mesh 100 extends beyond the second mesh 200 at one or both ends of the second mesh 200. In some embodiments, the second mesh 200 is longer than the first mesh 100 such that the second mesh 200 extends beyond the first mesh 100 at one or both ends of the first mesh 100. In some embodiments, the first mesh 100 and the second mesh 200 have generally the same length and/or are longitudinally aligned at one or both of their respective longitudinal ends.

Figure 2A:
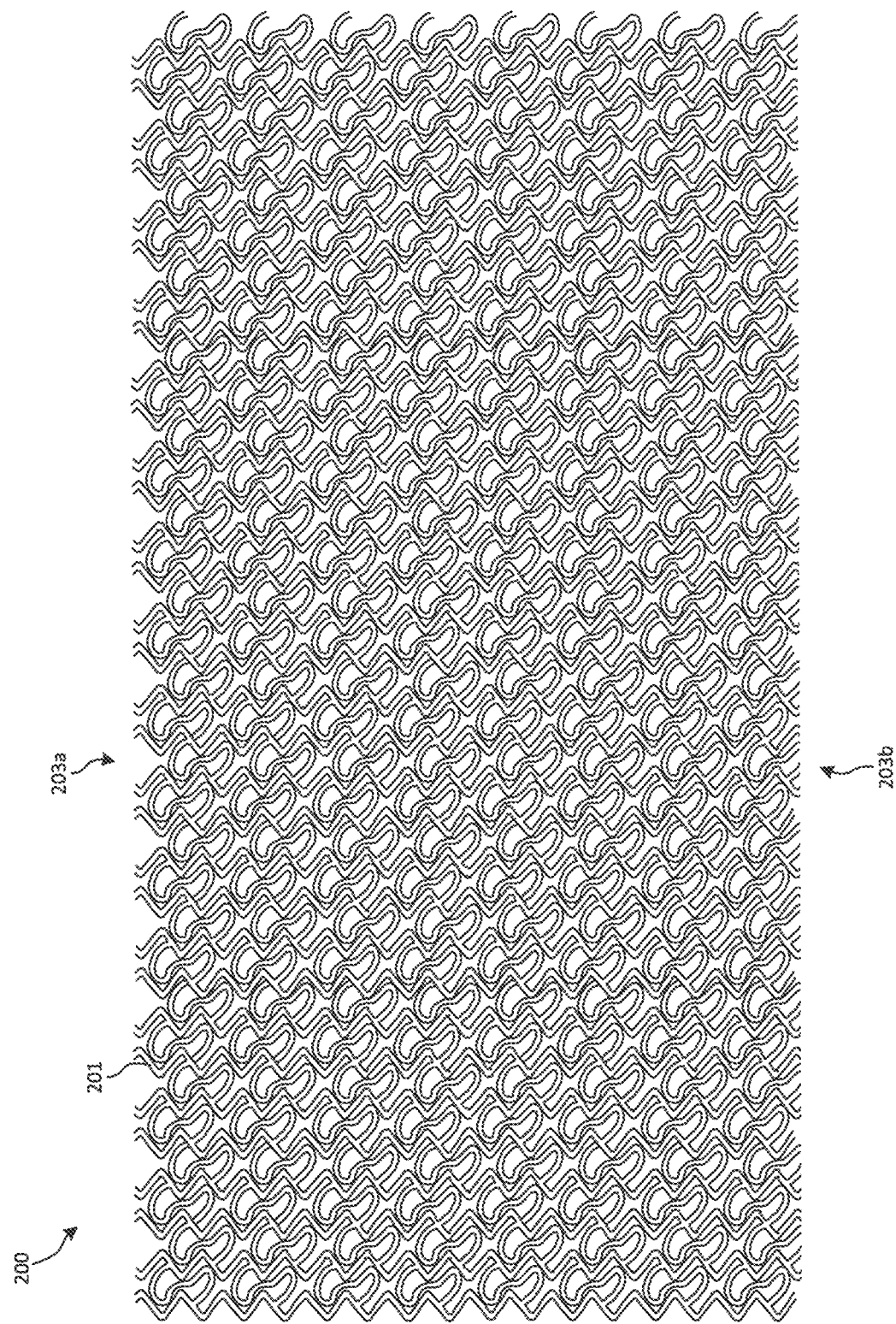
FIG. 2A is a plan view of the second mesh of the device shown in FIG. 1 in accordance with the present technology.

FIGS. 2A-2C are progressively zoomed-in plan views of the second mesh 200, shown isolated from the flow-diverting device 10 in an uncurled or laid-flat configuration. The second mesh 200 may be initially formed as a flat sheet 201 of material (FIG. 2A) having a pattern of struts 212 (FIGS. 2B and 2C) and bridges 214 (FIGS. 2B and 2C). The struts and bridges 212, 214 may be formed by depositing a thin film on a flat surface in the desired pattern, or by laser-cutting a desired pattern into a flat sheet of material. Additional details regarding the thin film deposition process and materials are discussed below under "Examples of Methods of Manufacture." The flat sheet 201 is then curled up into a generally tube-like shape (for example, as shown in FIG. 1) such that the longitudinal edges 203a, 203b (FIG. 2A) of the sheet 201 are positioned adjacent to or in contact with one another.

In the tube-like or coiled shape, the second mesh 200 can be circumferentially continuous or discontinuous. In those embodiments where the second mesh 200 is continuous, the longitudinal edges 203a, 203b can be joined (e.g., via laser welding) along all or a portion of their respective lengths. In those embodiments where the second mesh 200 is circumferentially discontinuous, the second mesh 200 can have a slit extending longitudinally along all or a portion of its length. In some embodiments, the longitudinal edges 203a, 203b of the second mesh 200 can overlap in the generally tubular configuration or be separated by a gap in the circumferential direction, or abut one another.

In some embodiments, the struts and bridges 212, 214 may be formed by depositing a thin film on the surface of a tubular frame in a desired pattern (e.g., via thin film deposition, vapor deposition, or combinations thereof), or by laser-cutting the desired pattern into a tubular sheet of material.

As best shown in FIG. 2C, the second mesh 200 may include a plurality of strut regions 204 (a few of which are labeled as 204a and 204b) and a plurality of bridge regions 205, both of which extend circumferentially around the second mesh 200 when the second mesh 200 is in the tubular configuration. The plurality of strut regions 204 include a plurality of struts 212, and the plurality of bridge regions 205 include a plurality of bridges 214 that extend between adjacent strut regions 204 (such as first strut region 204a and second strut region 204b). Within some or all of the strut regions 204, the struts 212 may be connected end-to-end such that the struts 212 are circumferentially disposed in a zig-zag or Z pattern (formed, e.g., of connected V's). The strut regions 204 may include struts 212 that are linear, curved, or both. Each strut region 204 may have 28-108 struts.

Adjacent struts 212 may connect to one another at apices 216, and the strut regions 204 may have first apices 218a that point towards the second end 10b of the device 10 (FIG. 1) and collectively define a first circumferential plane P1. The strut regions 204 may also have second apices 218b that point towards the first end 10a of the device 10 and collectively define a second circumferential plane P2.

Within some or all of the bridge regions 205, some or all of the bridges 214 include a first curved segment 220 and a second curved segment 222 such that the bridges 214 are generally S-shaped. As shown in FIG. 2C, in some embodiments the first and second curved segments 220, 222 may have opposing concavities. When the second mesh 200 is extended longitudinally, the bridges 214 can straighten relative to the longitudinal axis, allowing the strut regions 204 to move away from one another along the longitudinal axis of the mesh 200.

The ends of each of the bridges 214 connect to the struts 212 of adjacent strut regions 204. For example, in some embodiments, some or all of the bridges 214 within some or all of the bridge regions 205 connect a first strut 212a of a first strut region 204a to a second strut 212b of a second strut region 204b that is adjacent to the first strut region 204a. As shown in FIG. 2C, the first curved segment 220 of the bridge 214 may extend from a first end 224a at the first strut 212a across the first circumferential plane P1 and the second circumferential plane P2 towards the second strut region 204b. Likewise, the second curved segment 222 of the bridge 214 may extend from a second end 224b at the second strut 212b across the second circumferential plane P2 and the first circumferential plane P1 towards the first strut region 204a.

As shown in FIG. 2C, the first strut 212a may be located at a first side of a longitudinal plane P3 extending between a first apex 218a of the first strut region 204a and a second apex 218b of the second strut region 204b, where the second apex 218b is generally circumferentially aligned with and longitudinally adjacent to the first apex 218a. The second strut 212b may be located at a second side of the longitudinal plane P3 opposite the first side. Likewise, the first and second ends 224a, 224b of the bridge 214 may be connected to the first and second struts 212a, 212b, respectively, at locations along the first and second struts 212a, 212b that are away from the apices. In some embodiments, the first end 224a of the bridge 214 may be connected to a concave side 219b of a second apex 218b of the first strut region 204a, and the second end 224b of the bridge 214 may be connected to a concave side 219a of a first apex 218a of the second strut region 204b. In some embodiments, all of the apices 216 within some or all of the strut regions 204 are not connected to a bridge 214 such that all of the apices 216 within the strut region 204 are free.

In some embodiments, some or all of the bridges 214 may have one or more linear segments. In some embodiments, some or all of the bridges 214 comprise only linear segments and do not include curved segments. In those embodiments where the bridges 214 include only linear segments, the bridge 214 may form a zig-zag shape between its ends that are connected to the struts of the first and second strut regions. For example, the bridge 214 may include first, second, and third linear segments. The first linear segment may extend from a strut of the first strut region 204a towards the second strut region 204b (but does not connect to a strut of the second strut region 204b). The first linear segment may cross the first and second planes P1 and P2 (in that order). The second linear segment may extend from the unconnected end of the first linear segment back towards the first strut region 204a (but does not connect to a strut of the first strut region 204a). The second linear segment may cross the second plane P2, the third plane P3, then the first plane P1. The third linear segment may extend from the unconnected end of the second linear segment back towards the second strut region 204b and connects to a strut of the second strut region 204b. The third linear segment may cross the first and second planes P1 and P2 (in that order). The change in direction of the bridge 214 between the first and second segments creates a first indented segment of the bridge, and the change in direction of the bridge 214 between the second and third segments creates a second indented segment of the bridge 214 that faces away from the first indented segment. In any of the foregoing embodiments, some or all of the first, second, and third segments may be curved rather than linear. For example, in some embodiments, one or more of the bridges may have a first linear segment, a second curved segment rather than a second linear segment, and a third linear segment.

Figures 3A, 3B:
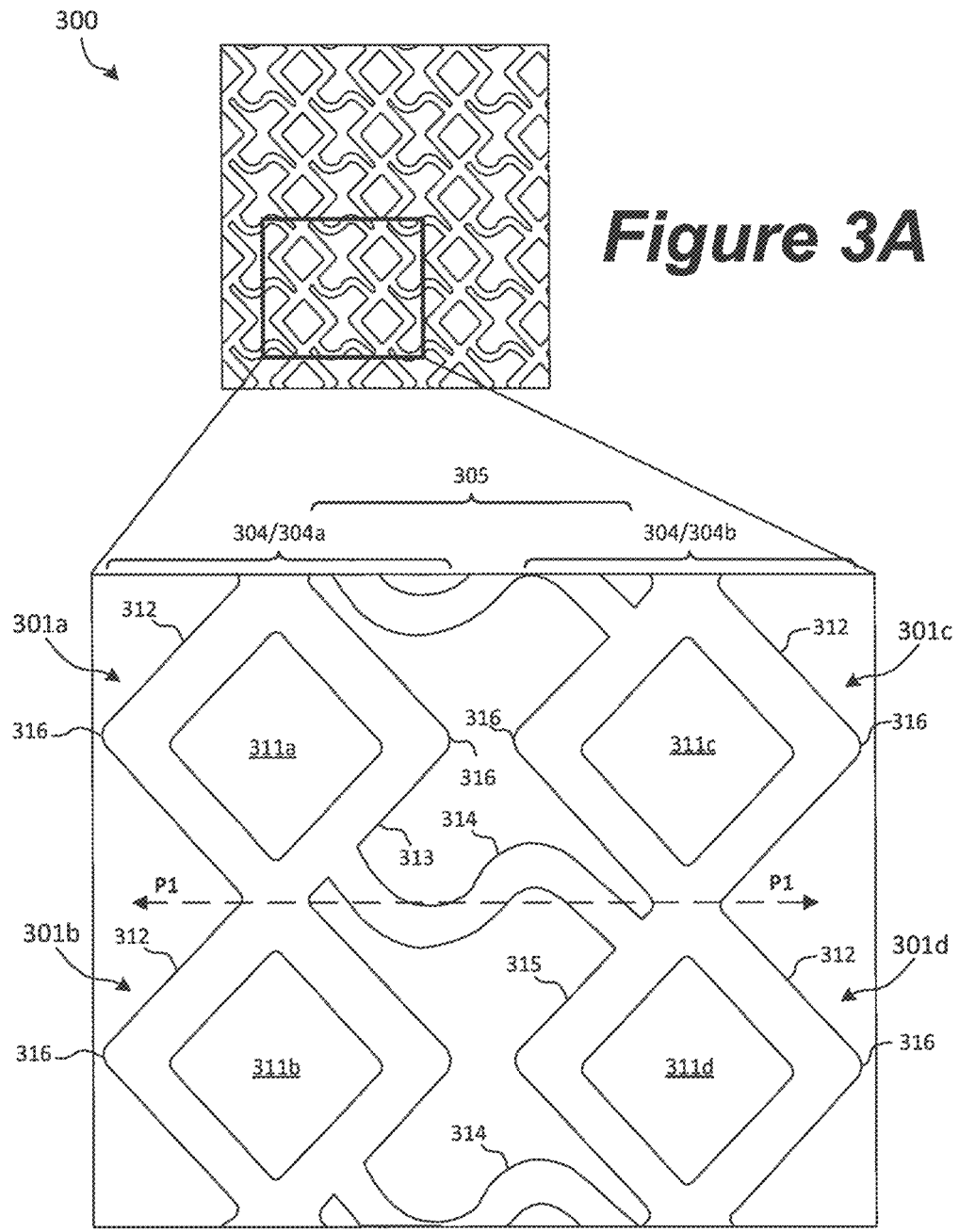
FIGS. 3A and 3B are enlarged views of portions of a second mesh for use with the flow-diverting devices of the present technology.

FIGS. 3A and 3B are plan views of another embodiment of a second mesh 300 for use as a standalone flow-diverting device or with the flow-diverting devices disclosed herein. In FIGS. 3A and 3B, the second mesh 300 is shown in an uncurled or laid-flat configuration. The second mesh 300 may be formed as discussed above with reference to the second mesh 200. The second mesh 300 may include a plurality of strut regions 304 (labeled individually as first and second strut regions 304a, 304b) and a plurality of bridge regions 305. Both the plurality of strut regions 304 and the plurality of bridge regions 305 may extend circumferentially about the second mesh 300. Each of the strut regions 304 include a plurality of struts 312 and a plurality of apices 316 at which each of the struts 312 is coupled to another strut 312. As shown in FIG. 3B, within some or all of the strut regions 304, some or all of the plurality of struts 312 may form a plurality of circumferentially disposed closed polygonal cells 301 (several labeled individually as 301a-301d) defined by the struts 312. Each of the polygonal cells 301 defines a corresponding polygonal interior region 311a-311d. The polygonal cells 301 may provide a pore size that is 5-450 µm. A pore size can be measured via a maximum inscribed circle technique.

In some embodiments, at least one of the polygonal cells 301 is a quadrilateral. In some embodiments, at least one of the polygonal cells 301 is diamond-shaped.

Each of the plurality of bridge regions 305 extend between adjacent strut regions 304 and include a plurality of bridges 314. Some or all of the bridges 314 may be sinusoidal. Within some or all of the bridge regions 305, some or all of the bridges 314 include a first end coupled to a first closed polygonal cell 301 of a first strut region 304a at a location away from the apices 316 of the first strut region 304a, and a second end coupled to a second closed polygonal cell 301 of a second strut region 304b adjacent to the first strut region 304a at a location away from the apices 316 of the second strut region 304b. In some embodiments, within some or all of the strut regions 304, some or all of the closed polygonal cells 301 are coupled to an adjacent closed polygonal cell 300 at one of the apices 316.

In any of the embodiments disclosed herein, some or all of the bridges and/or some or all of the struts can comprise a radiopaque marker. The radiopaque marker can be disposed on a substantially straight section of a bridge and/or a strut, so the radiopaque marker is predominantly not subject to bending or flexing. For example, the radiopaque marker(s) can be disposed a distance away from an apex. The radiopaque marker(s) can be formed on the bridges and/or the struts by a process that is the same or different than a process used to form the bridges and/or the struts, which is discussed further herein.

In any of the embodiments disclosed herein, the second meshes can provide a porosity of 5-95%.

In any of the embodiments disclosed herein, within some or all of the bridge regions, some or all of the bridges can be non-branching between the ends of the bridge. Within some or all of the bridge regions, some or all of the bridges can be unconnected to any other bridge. Each bridge region can have, e.g., 28-108 bridges.

The respective thicknesses of the struts and the bridges disclosed herein can be measured as a dimension that is orthogonal to a central axis when the flow-diverting device and/or second mesh is considered in a tubular shape or as a dimension that is orthogonal to a plane of the device when represented as laid-flat. The length of a strut can be measured as a distance extending between ends of a strut, where the ends connect to another structure. The length of a bridge can be measured as a distance extending between its ends along its central longitudinal axis. The respective widths of the struts and the bridges can be measured as the distance that is generally orthogonal to the length and thickness. The width and length of a strut can contribute to a surface coverage and porosity of the device 10 and/or second mesh. According to some embodiments, a thickness of the struts and/or the bridges disclosed herein can be 5-50 µm, for example 50 µm. According to some embodiments, a width of the struts and/or the bridges disclosed herein can be 5-50 µm, for example 50 µm.

Some or all of the struts and/or bridges disclosed herein can have a square cross-section. However, some or all of the struts and bridges discloses herein may have other suitable cross-sectional shapes, such as rectangular, polygonal, round, ovoid, elliptical, or combinations thereof.

For any of the second mesh embodiments disclosed herein, one or more of the bridges within a given bridge region can have the same or different length, width, thickness, as one or more of the other bridges within the same bridge region. In some embodiments, all of bridges of all of the bridge regions can have the same length, width, and/or thickness. In some embodiments, all of bridges of one or more bridge regions can have a different length, width, and/or thickness as all of the bridges of some or all of the other bridge regions.

For any of the second mesh embodiments disclosed herein, one or more of the struts within a given strut region can have the same or different length, width, thickness, as one or more of the other struts within the same strut region. In some embodiments, all of struts of all of the strut regions can have the same length, width, and/or thickness. In some embodiments, all of struts of one or more strut regions can have a different length, width, and/or thickness as all of the struts of some or all of the other strut regions.

Examples of Methods of Manufacture

According to some embodiments, the second meshes disclosed herein can be formed by a photolithography process. A substrate can be provided with a base for supporting the formation of the expandable device. The base (e.g., copper) can be used temporarily as a buffer between the substrate and a primary material used to form the expandable device. After the base is provided on the substrate, the primary material is provided thereon, for example by vapor deposition. The primary material, such as a metal or alloy (e.g., nitinol) can be provided as a thin film of substantially uniform thickness. For example, the thin film can have a thickness no greater than 4 mm. In some embodiments, the thin film of the second mesh can have a thickness of 0.001-4 millimeters, and in some embodiments, the thin film can have a thickness of 0.01-3 mm, or 0.001-2 mm, or 0.001-1 mm, or 0.001-0.1 mm, or 0.001-0.01 mm. Portions of the primary material can be removed to form the structure of the expandable device. For example, a photomask, based on a strut pattern, can be used to selectively expose portions of the primary material to light and etch the primary material into the desired shape for the expandable device. Alternatively or in combination, a chemical agent can be used to remove the portions of the primary material that are not protected by a photoresist. The base can then be eroded to separate the expandable device from the substrate. The expandable device can be further treated to form a desired shape (e.g., tubular) and have the desired heat set and/or shape memory properties.

In some embodiments, a radiopaque material is disposed on the deposited metal or alloy. In some embodiments, the radiopaque material in disposed only in areas of low stress concentration.

Examples of Methods of Use

As mentioned elsewhere herein, the present disclosure includes methods of treating a vascular condition, such as an aneurysm, with any of the embodiments of the expandable devices disclosed herein. The expandable device could be deployed across the neck of an aneurysm and its flow-diverting properties employed to impede blood flow between the aneurysm and the parent vessel, cause the blood inside the aneurysm to thrombose, and lead to healing of the aneurysm. The expandable devices disclosed herein may also be used to treat other vascular defects. For example, the expandable devices of the present technology may be used to remove clot material from a blood vessel (e.g., as a thrombectomy device).

In order to implant any of the flow-diverting devices and/or second meshes (referred to generically as "expandable devices") disclosed herein, the expandable device can be mounted in a delivery system. For example, the first or second end region of the expandable device can be configured to be detachably coupled to an elongate delivery system. Generally, the delivery system can comprise an elongate core member that supports or contains the expandable device, and both components can be slidably received in a lumen of a microcatheter (e.g., a 0.021" or 0.027" microcatheter) or other elongate sheath for delivery to any region to which the distal opening of the microcatheter can be advanced. The core member is employed to advance the expandable device through the microcatheter and out the distal end of the microcatheter so that the expandable device is allowed to self-expand into place in the blood vessel, across an aneurysm or other treatment location. Accordingly, a vascular treatment apparatus can comprise a delivery system, such as any of the delivery systems described herein, and an expandable device, such as any of the flow-diverting devices and/or second meshes described herein, mounted in or on the delivery system.

A treatment procedure can begin with obtaining percutaneous access to the patient's arterial system, typically via a major blood vessel in a leg or arm. A guidewire can be placed through the percutaneous access point and advanced to the treatment location, which can be in an intracranial artery, or any neurovascular artery, peripheral artery or coronary artery. (As configured for neurovascular use, any of the expandable devices disclosed herein can have, e.g., a diameter of 2-8 mm in the relaxed state or the expanded state; such expandable devices used in the peripheral or coronary vasculature can have, e.g., a diameter of 1-20 mm in the relaxed state or the expanded state.) The microcatheter is then advanced over the guidewire to the treatment location and situated so that a distal open end of the guidewire is adjacent to the treatment location. The guidewire can then be withdrawn from the microcatheter and the core member, together with the expandable device mounted thereon or supported thereby, can be advanced through the microcatheter and out the distal end thereof. The expandable device can then self-expand into apposition with the inner wall of the blood vessel. Where an aneurysm is being treated, the expandable device is placed across the neck of the aneurysm so that a sidewall of the expandable device separates the interior of the aneurysm from the lumen of the parent artery.

Once the expandable device has been placed, the core member and microcatheter are removed from the patient. The expandable device sidewall can now perform a flow-diverting function on the aneurysm, thrombosing the blood in the aneurysm and leading to healing of the aneurysm.

CONCLUSION

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

It is understood that the specific order or hierarchy of steps in the processes disclosed is an illustration of exemplifying approaches. Based upon design preferences, it is understood that the specific order or hierarchy of steps in the processes may be rearranged. Some of the steps may be performed simultaneously. Various methods are disclosed presenting elements of the various steps in a sample order, and are not meant to be limited to the specific order or hierarchy presented.

Furthermore, to the extent that the term "include," "have," or the like is used herein, such term is intended to be inclusive in a manner similar to the term "comprise" as "comprise" is interpreted when employed as a transitional word in a Clause.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The numbered clauses and their equivalents are intended to cover such forms or modifications as would fall within the scope and spirit of the subject technology.

I claim:

1. An expandable device comprising:
a plurality of strut regions extending circumferentially about the expandable device, each of the strut regions including a plurality of struts and a plurality of apices, each of the struts extending between adjacent apices and each of the struts being linear along an entire length of the respective strut, wherein each of the struts is coupled to an adjacent strut at one of the plurality of apices so as to form a zig-zag pattern of connected V-shapes, wherein the plurality of strut regions includes a first strut region having first struts and a second strut region having second struts, the first strut region adjacent the second strut region, and wherein (a) the first strut region comprises a first plurality of apices extending towards the second strut region and defining a first circumferential plane, and (b) the second strut region comprises a second plurality of apices extending towards the first strut region and defining a second circumferential plane; and
a plurality of bridge regions extending between adjacent strut regions and including a plurality of bridges, wherein each of the bridges includes a first curved segment and a second curved segment having opposing concavities,
wherein each of the bridges extends between a first end disposed at one of the first struts of the first strut region and a second end disposed at one of the second struts of the second strut region such that each of the first curved segments of the bridges extend across the first circumferential plane towards the second strut region and each of the second curved segments of the bridges extend across the second circumferential plane towards the first strut region, and
wherein, each of the first struts is attached to and extends directly from one of the first apices in a first circumferential direction and each of the second struts is attached to and extends directly from one of the second apices in a second circumferential direction opposite the first circumferential direction, and wherein individual ones of the first apices are circumferentially aligned with individual ones of the second apices.

2. The expandable device of claim 1 wherein the plurality of bridges comprises a plurality of s-shaped bridges.

3. The expandable device of claim 1 wherein each of the first curved segments intersect the second circumferential plane at two different points, and wherein each of the second curved segments intersect the first circumferential plane at two different points.

4. The expandable device of claim 1 wherein each of the bridges is coupled to a strut region at a location spaced apart from the apices of the strut region.

5. The expandable device of claim 1 wherein the expandable device is a mesh.

6. The expandable device of claim 1 wherein the expandable device is a laser-cut sheet.

7. The expandable device of claim 1 wherein the expandable device is non-braided.

8. The expandable device of claim 1, wherein the expandable device comprises a thin film in which the strut regions and bridge regions are formed.

9. The expandable device of claim 8, wherein the thin film is formed via a deposition process.

10. The expandable device of claim 9, wherein the thin film is no more than 4 millimeters in maximum thickness.

11. The expandable device of claim 1 wherein each of the first curved segments intersect the second circumferential plane at two different points, and wherein each of the second curved segments intersect the first circumferential plane at two different points, wherein the two different points are located at one side of a longitudinal plane defined by the first apices and the second apices.

12. The expandable device of claim 1 wherein the each of the struts has a first terminus at one of the apices and a second terminus at another one of the apices, the entire length of the strut being between the first terminus and the second terminus.

13. The expandable device of claim 1 wherein:
each of the first struts are attached to one of the first apices and extend directly from the one of the first apices in a first direction, the first direction having a first circumferential component and a first longitudinal component, and
each of the second struts are attached to one of the second apices and extend directly from the one of the second apices in a second direction, the second direction having a second circumferential component, and
wherein the second circumferential component is opposite the first circumferential component.

14. An expandable device comprising:
a first tubular mesh defining a lumen therethrough, the first tubular mesh comprising:
a plurality of strut regions extending circumferentially about the expandable device, each of the strut regions including a plurality of struts and a plurality of apices, each of the struts extending between adjacent apices and each of the struts being linear along an entire length of the respective strut, wherein each of the struts is coupled to an adjacent strut at one of the plurality of apices to so as to form a zig-zag pattern of connected V-shapes, wherein the plurality of strut regions includes a first strut region having first struts and a second strut region having second struts, the first strut region adjacent the second strut region, and wherein the first strut region comprises a first plurality of apices extending towards the second strut region and defining a first circumferential plane, the second strut region comprising a second plurality of apices extending towards the first strut region and defining a second circumferential plane; and
a plurality of bridge regions extending between adjacent strut regions and including a plurality of bridges, wherein each of the bridges includes a first indented segment and a second indented segment having opposing indentions,
wherein each of the bridges extends between a first end disposed at one of the first struts of the first strut region and a second end disposed at one of the second struts of the second strut region such that each of the first indented segments of the bridges extends across the first circumferential plane towards the first strut region and each of the second indented segments of the bridges extend across the second circumferential plane towards the second strut region, and
wherein, each of the first struts is attached to and extends directly from one of the first apices in a first circumferential direction and each of the second struts is attached to and extends directly from one of the second apices in a second circumferential direction opposite the first circumferential direction, and wherein individual ones of the first apices are circumferentially aligned with individual ones of the second apices; and
a second tubular mesh, at least a portion of which is positioned within the lumen of the first tubular mesh.

15. The expandable device of claim 14 wherein both of the first tubular mesh and the second tubular mesh are non-braided.

16. The expandable device of claim 14 wherein the second tubular mesh is a tubular weave.

17. The expandable device of claim 16 wherein the tubular weave is formed of a single wire.

18. The expandable device of claim 14 wherein the second tubular mesh is a braid.

19. The expandable device of claim 14 wherein the first tubular mesh comprises a thin film in which the strut regions and bridge regions are formed.

* * * * *

UNITED STATES PATENT AND TRADEMARK OFFICE
CERTIFICATE OF CORRECTION

PATENT NO. : 10,835,398 B2
APPLICATION NO. : 15/802679
DATED : November 17, 2020
INVENTOR(S) : Animesh Choubey It is certified that error appears in the above-identified patent and that said Letters Patent is hereby corrected as shown below:

In the Claims

In Column 19, in Claim 14, Line 35, delete "to so as" and insert -- so as --, therefor.

In Columns 19 and 20, in Claim 14, Lines 43 and 1, delete "comprising" and insert -- comprises --, therefor.

Signed and Sealed this
Nineteenth Day of January, 2021

Andrei Iancu
*Director of the United States Patent and Trademark Office*